US00RE50617E

(19) United States
(12) Reissued Patent
Deshpande et al.

(10) Patent Number: US RE50,617 E
(45) Date of Reissued Patent: Oct. 7, 2025

(54) METHOD FOR STRESS MANAGEMENT AND OVERALL HEALTH STATUS IMPROVEMENT AND COMPOSITIONS USED THEREIN

(71) Applicant: OMNIACTIVE HEALTH TECHNOLOGIES LIMITED, Maharashtra (IN)

(72) Inventors: Jayant Deshpande, Congers, NY (US); James M Stringham, Durham, NC (US); Vijaya Juturu, Morristown, NJ (US)

(21) Appl. No.: 17/687,712

(22) Filed: Mar. 7, 2022

Related U.S. Patent Documents

Reissue of:
(64) Patent No.: 10,583,095
Issued: Mar. 10, 2020
Appl. No.: 15/058,821
Filed: Mar. 2, 2016

U.S. Applications:
(60) Provisional application No. 62/126,971, filed on Mar. 2, 2015.

(51) Int. Cl.

| | |
|---|---|
| ***A61K 31/047*** | (2006.01) |
| ***A61K 31/07*** | (2006.01) |
| ***A61P 25/00*** | (2006.01) |
| ***A61P 27/00*** | (2006.01) |
| ***G01N 21/59*** | (2006.01) |
| ***G01N 30/00*** | (2006.01) |
| ***G01N 30/88*** | (2006.01) |
| ***G01N 33/487*** | (2006.01) |
| ***G01N 33/74*** | (2006.01) |

(52) U.S. Cl.
CPC ..... *A61K 31/047* (2013.01); *A61K 31/07* (2013.01); *A61P 25/00* (2018.01); *A61P 27/00* (2018.01); *G01N 21/5907* (2013.01); *G01N 30/00* (2013.01); *G01N 33/487* (2013.01); *G01N 33/743* (2013.01); *G01N 30/88* (2013.01); *G01N 2030/8813* (2013.01); *G01N 2800/52* (2013.01)

(58) Field of Classification Search
CPC ..... A61K 31/047; A61P 25/00
See application file for complete search history.

(56) References Cited

U.S. PATENT DOCUMENTS

| | | | |
|---|---|---|---|
| 5,976,568 | A | 11/1999 | Riley |
| 7,869,636 | B2 | 1/2011 | Korotkov |
| 8,212,063 | B2 | 7/2012 | Kumar et al. |
| 8,658,128 | B2 | 2/2014 | Altschul et al. |
| 8,962,043 | B2 | 2/2015 | Nolan et al. |
| 10,583,095 | B2 | 3/2020 | Deshpande et al. |
| 2011/0065805 | A1 | 3/2011 | Kumar et al. |
| 2011/0144200 | A1 | 6/2011 | Eidenberger |
| 2012/0232162 | A1 | 9/2012 | Goralczyk et al. |
| 2012/0258168 | A1 | 10/2012 | Montesinos |
| 2014/0221487 | A1 | 8/2014 | Renzi et al. |

FOREIGN PATENT DOCUMENTS

| | | | |
|---|---|---|---|
| WO | 2007/029008 | | 3/2007 |
| WO | 2007029008 | A2 | 3/2007 |
| WO | 2012139132 | | 10/2012 |
| WO | 2012139132 | A1 | 10/2012 |
| WO | 2014155189 | | 10/2014 |
| WO | 2014155189 | A1 | 10/2014 |

OTHER PUBLICATIONS

Hansel et al. Neuroscience and Behavioral Reviews.vol. 35, pp. 115-121 (Year: 2010).*
Mitoma et al. Progress in Neuro-Psychopharmacology & Biological Psychiatry vol. 32. pp. 679-685 (Year: 2008).*
Meschino, Central Serous Retinopathy: Common Causes and Nutritional Management, 2013, Meschino Health, pp. 1-7.*
NEI, For the Public: What the AREDS Means for You, 2013, NEI, pp. 1-5.*
International Search Report and Written Opinion for PCT/IB2016/051185, dated Jul. 26, 2016, 8 pages.
Choi et al., "Curcumin inhibits hypoxia-inducible factor-1 by degrading aryl hydrocarbon receptor nuclear translocator: A mechanism of tumor growth inhibition", Molecular Pharmacology, Jul. 31, 2016, 43 pages.
Kaliora et al., "Dietary antioxidants in preventing atherogenesis", Atherosclerosis, vol. 187, 2006, pp. 1-17.
Heinrich et al., "Supplementation with b-Carotene or a Similar Amount of Mixed Carotenoids Protects Humans from UV-Induced Erythema", The Journal of Nutrition, Oct. 10, 2002, pp. 98-101.
Elizabeth J. Johnson, "A possible role for lutein and zeaxanthin in cognitive function in the elderly1-5", The American Journal of Chemical Nutrition, vol. 96, 2012, pp. 1161-1165.
Feeney et al., "Low macular pigment optical density is associated with lower cognitive performance in a large, population-based sample of older adults", Neurobiology of Aging, vol. 34, 2013, pp. 2449-2456.

(Continued)

*Primary Examiner* — Padmashri Ponnaluri
(74) *Attorney, Agent, or Firm* — Carlson, Caspers, Vandenburgh & Lindquist, P.A.

(57) ABSTRACT

Carotenoid compositions are described for management, treatment, and/or prevention of stress by reducing cortisol levels and/or improving distribution and/or density of macular pigment and thus improving overall health status. More particularly, a subject in need thereof for the method has disturbed macular pigment optical density or increased levels of cortisol as markers of psychological and physiological stress. Methods are also described of administering macular carotenoid compositions in daily doses of at least or about 0.005 mg/kg body weight of lutein, and at least or about 0.001 mg/kg body weight of meso-zeaxanthin and zeaxanthin isomer along with at least one food grade excipient and evaluating overall health status. The composition may be derived from plant extract containing xanthophylls and/or xanthophylls esters. The composition also reduces cortisol levels in the blood and relieves physiological stress, thus improving overall health status of a subject in need thereof.

18 Claims, 8 Drawing Sheets

(56) References Cited

OTHER PUBLICATIONS

Vishwanathan et al., "Macular pigment optical density is related to cognitive function in older people", Age and Ageing, vol. 43, 2014, pp. 271-275.
Gao et al., Lutein and zeaxanthin supplementation reduces H2O2-induced oxidative damage in human lens epithelial cells, Molecular Vision, vol. 17, 2011, pp. 3180-3190.
Extended European Search Report (EESR), issued in the corresponding European patent application No. 16758534.8, dated Oct. 5, 2018, 9 pages.
Cavar et al., "Metabolic Risk Factors, Coping with Stress, and Psychological Well-Being in Patients with Age-Related Macular Degeneration", Acta Clinica Croatica, vol. 53, No. 1, pp. 79-87, 2014.

* cited by examiner

METHOD FOR STRESS MANAGEMENT AND OVERALL HEALTH STATUS IMPROVEMENT AND COMPOSITIONS USED THEREIN

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE TO RELATED APPLICATIONS*

*This application is a reissue application for U.S. Pat. No. 10,583,095, issued on Mar. 10, 2020, from U.S. application Ser. No. 15/058,821, filed Mar. 2, 2016, which claims the benefit of U.S. Provisional Application No. 62/126,971, filed on Mar. 2, 2015; the disclosures of all of which are hereby incorporated by reference in their entirety.*

FIELD

Methods herein are described for managing stress and improving overall health status by administering macular carotenoid compositions containing an effective daily dose, to a subject in need thereof. The macular carotenoid compositions herein are comprised of xanthophyll carotenoids selected from the group of lutein, zeaxanthin, meso-zeaxanthin, enantiomers, metabolites, esters, salts, derivatives either alone, or in combinations thereof, along with one or more food grade excipients, such as fat, fatty acid, oil, antioxidant, vitamin, and the like and the combinations thereof. More particularly, methods herein are described and include use of the macular carotenoid compositions herein for identifying a subject in need thereof. Methods herein are described and include administering a daily dose of at least 0.005 mg/kg of lutein and at least 0.001 mg/kg body weight of zeaxanthin isomer(s), along with at least one food grade excipient. The lutein can be one or more isomers of lutein, including trans-lutein (t-lutein). The zeaxanthin isomer(s) can include one or more isomers of zeaxanthin, such isomers including meso-zeaxanthin or R,R-zeaxanthin, or both of these isomers. Methods herein are described and include evaluating overall health status based on administration of the macular carotenoid compositions. The stress to be managed includes but is not limited to physiological, psychological, chronic or the like or in a combination thereof. Methods described herein increase serum levels of lutein and zeaxanthin and improve macular pigment optical density (MPOD) at a lower dose of composition. The macular carotenoid compositions improve density and/or distribution of macular pigments in eyes, thus relieve psychological stress in a subject. The methods also comprise administering the macular carotenoid compositions to reduce oxidative stress and inflammation afforded by relatively high circulating levels of lutein and zeaxanthin and thus reduce stress, cortisol levels and anxiety. The method described herein particularly useful for managing psychological, physiological, and chronic stress and can be employed for management of the stress as well as management of stress and risk factors associated with the stress and improving overall health status of a subject, by administering the macular carotenoid composition in an effective daily dose.

BACKGROUND

The term "stress" describes mental or physical reactions due to day to day life and/or clinical associated conditions including chronic disease conditions and/or not limited to what people feel when they are under mental, physical, social or emotional pressure. Based on the conditions creating stress, it may be categorized mainly as psychological or physiological stress, in a subject. Although it is normal to experience some type of stress from time to time, people or an animal who experience a high level of physiological or psychological stress or who experience it repeatedly over a long period of time may develop mental and/or physical health problems.

Such stress can be caused both by daily responsibilities and routine events, as well as by more unusual events, such as a trauma or illness in a mammal including but not limited to him/her/oneself or a close family member. It can sometimes help to motivate people to finish a task, or perform well. But stress can also be harmful if one becomes overstressed as the stress interferes with the ability to get on with normal life for too long. One may feel tired, unable to concentrate or may easily become irritated. Stress can also damage an individual's physical health. When people feel that they are unable to manage or control changes caused by any illness or daily life activities, they experience physiological as well as psychological stress. This has become increasingly recognized as a factor that can reduce the quality of life of patients suffering from chronic diseases such as cancer. There is even some evidence that extreme stress is associated with poorer clinical outcomes. Clinical guidelines are available to help doctors and nurses assess levels of stress and help patients manage it. Some studies have indicated a link between various psychological factors and an increased risk of developing cancer.

If one faces a stressful event, the body responds by activating the nervous system and releasing hormones such as adrenalin and cortisol. These hormones cause physiological changes in the body which help one to react quickly and effectively to get through the stressful situation. This is sometimes called the 'fight or flight' response. The hormones increase one's heart rate, breathing, blood pressure, metabolism, and muscle tension. One's pupils dilate and our perspiration rate increases. While these physical changes help one try to meet the challenges of the stressful situation, they can cause other physical or psychological symptoms. It can be linked to headaches, an upset stomach, back pain, and trouble sleeping. It can weaken a person's immune system, making it harder to fight off diseases. If a person already has a health problem, stress may make it worse. It can make a person moody, tense, or depressed. The relationships with others may suffer, and a person would not do well at work. Hence it is very important to manage all types of stress for leading a healthy life.

Stress management encompasses techniques intended to equip a subject with effective coping mechanisms for dealing with physiological and psychological stress. Techniques of stress management include self-understanding, self-management (e.g. becoming better-organized), conflict resolution, adopting a more positive attitude, breathing exercises, meditation, exercises, altering the diet, medical treatment (e.g. anti-anxiety drugs) and taking more rest regularly and effectively. A good diet with a well-balanced nutrition is very important for achieving a stress resistant body. (Ref: Combating Stress with a Balanced Nutritional Diet: By Jayne Ritchie-Stress Management Society and Bodychef).

Diets rich in vitamins, minerals and essential amino acids can be helpful in this context.

Macular carotenoids, especially xanthophylls, such as lutein, zeaxanthin isomers (RR-Zeaxanthin/RS-meso-zeaxanthin), meso-zeaxanthin and the like and their enantiomers, metabolites, esters, salts, derivatives either alone or in combination are considered to be important nutritional elements for a human body. These carotenoids effectively protect biological tissue in a mammal such as retinas of eyes by acting as an antioxidant, where the carotenoids accumulate in very high densities in the macula. This leads to a significant reduction of a risk of developing diseases, including age-related macular degeneration (AMD). Macular carotenoids' antioxidant function also appears to benefit cardiovascular health, skin health, and brain health. Indeed, higher levels of carotenoids such as lutein and zeaxanthin, presumably through anti-inflammatory action (Choi et al. 2006) have been associated with reduced atherosclerosis (Kailora, 2006), protection from UV-induced erythema (Heinrich et al. 2003), and significantly better cognitive performance in the elderly (Johnson et al. 2012; Feeney et al. 2013; Vishwanathan et al. 2014).

Joanne et al (Neurobiology of Aging Volume 34, Issue 11, November 2013, Pages 2449-2456) relates to the relationship between a macular pigment, such as lutein (L), zeaxanthin (Z), and meso-zeaxanthin (MZ), and cognitive function in adults aged ≥50 years. Xanthophyll carotenoids were found to have an impact on a cognitive function.

Johnson et al. (Am J Clin Nutr. 2012 November; 96(5): 1161S-5S. doi: 10.3945/ajcn.112.034611. Epub 2012 Oct. 10) relates to a relation between cognition and lutein and zeaxanthin concentrations in the brain tissue of decedents from a population-based study. It was found that zeaxanthin concentrations in brain tissue were significantly related to levels of a global cognitive function, memory retention, verbal fluency, and dementia severity after adjustment for age, sex, education, hypertension, and diabetes.

Gao S et al. (Mol Vis. 2011; 17: 3180-90. Epub 2011 Dec. 7) relates to lutein or zeaxanthin supplementation to protect lens protein, lipid, and DNA from oxidative damage and to improve the intracellular redox status upon oxidative stress. The data implies that sufficient intake of lutein and zeaxanthin may reduce the risk for senile cataract via protecting the lens from oxidative damage.

PCT patent application published as WO 2012/139132A1 relates to a composition to promote ocular health. The composition includes amounts of vitamin A; vitamin C; vitamin D; vitamin E; zinc; copper; selenium; non-vitamin A carotenoids, which include lutein and zeaxanthin; omega-3 fatty acids, which include eicosapentaenoic acid and docosahexaenoic acid; taurine; alpha-lipoic acid; pine bark extract; astaxanthin; and Piper spp. extract. The reference describes a method of a treatment for a subject experiencing oxidative or visual stress related degradation to the eye.

U.S. patent application publication 2012/0232162A1 relates to a method of enhancing an aspect of memory in a healthy individual, wherein the aspect of memory is selected from the group consisting of: associative memory, spatial memory and memory under stress comprising: administering a composition consisting of: a) an effective amount of either lutein or the combination of lutein and zeaxanthin; and b) an appropriate carrier; and observing the enhanced associative memory, spatial memory or memory under stress.

U.S. Pat. No. 5,976,568 relates to a total modular system of multivitamin and mineral supplementation for improving public health. One of the modular systems is a stress module oral dosage composition containing: about 2500 IU of Beta Carotene, about 500 IU of Alpha Carotene, about 400 mcg of Lutein, about 400 mcg of Lycopene, about 20 mcg of Zeaxanthin, about 1,5000 IU of Vitamin A, about 7.5 mg of Vitamin $B_1$, about 12.5 mg of Vitamin $B_2$, about 40 mg of Niacinamide, about 10 mg of Pantothenic Acid, about 15 mg of Vitamin $B_6$, about 300 mcg of Biotin, about 6 mcg of Vitamin $B_{12}$, about 600 mg of Vitamin C, about 30 IU of Vitamin E, about 450 mg of Calcium, about 70 mcg of Chromium, about 0.5 mg of Copper, about 3 mg of Iron, about 200 mg of Magnesium, about 50 mcg of Selenium, and about 7 mg of Zinc. The modular system is directed towards supplying the needs to persons during periods of physical and emotional stress, and for support for the immune system during and recovering from illness by using a combination of multivitamins and essential nutrients. The study focuses on the support of the immune system using a combination of multivitamins and minerals. The focus is not on any effect of any particular individual ingredient on physical and emotional stress.

Although many health benefits of the macular carotenoid rich diet are known, none of the references focus on their role in managing physiological and psychological stress. Stress is a health problem faced by the population at large due to a busy life style and it affects many vital organs of the body, such as the brain and nerves, heart, muscles and joints, digestive system and reproductive system, thus increasing burden on health system. Even though different exercises and counseling techniques are available for managing the stress, none of these is proven to be very effective for improving overall health status of a subject experiencing, suffering from, or likely to develop physiological or psychological stress. Thus there is a need of having an effective solution for managing physiological, psychological and chronic stress, particularly through dietary supplementation, which is convenient for the person in need of the managing the stress.

SUMMARY

Taking into account several health benefits and high tissue densities achieved by carotenoids in different body tissues, it would be highly desirable to evaluate effects of carotenoids on improving overall health status by managing physiological and psychological variables causing the stress, in order to provide alternate, effective, and safe solutions to address problems of managing stressful conditions. Chronic psychological stress is fairly common in modern society, and may lead to many undesirable physical and psychological health outcomes. Stress in the form of anxiety or depression can affect behavior of an individual, thus affecting the performance and sometimes can turn to fatal conditions. Stress can lead to changes in the serum level of many hormones including, for example but not limited to glucocorticoids, insulin, vasopressin, catecholamines, growth hormone and/or prolactin. It can also alter the clinical status of many preexisting endocrine disorders, such as but not limited to the precipitation of adrenal crisis and thyroid storm. Stress can enhance secretion of a number of hormones including glucocorticoids, insulin, vasopressin, catecholamines, growth hormone and prolactin. The increase of the hormone levels in subjects such for example a human and/or other mammals can improve mobilization of energy sources and allows them to adapt to their new circumstances.

Evidence of the protective role of macular carotenoids in maintaining eye health through the effect of the macular carotenoids as an antioxidant and anti-inflammatory has been presented. Embodiments herein are directed to their applications for management of stress by establishing co-relation(s) between improvement of distribution and density of a macular pigment in eyes and their macular carotenoids effect on relieving stress in a subject in need thereof, thus resulting into improving overall health status.

An embodiment herein is directed to a method of identifying a subject in need thereof for stress management, by administering a macular carotenoid composition to such a subject in an effective daily dose, and co-relating stress with a measured level of optical density and/or distribution of macular pigments.

An embodiment herein is directed to a method of identifying a subject in need thereof to increase macular pigment optical density (MPOD), by administering a macular carotenoid composition at a daily dose of at least 0.005 mg/kg of lutein, and at least 0.001 mg/kg body weight of zeaxanthin isomer(s) to such a subject, and correlating with a measured level of optical density and/or distribution of macular pigments.

The lutein in macular carotenoid compositions herein can be one or more isomers of lutein, including trans-lutein (t-lutein). The zeaxanthin isomer(s) in macular carotenoid compositions herein can include one or more isomers of zeaxanthin, such isomers including meso-zeaxanthin or R,R-zeaxanthin, or both of these isomers.

In an embodiment, the macular carotenoid composition is administered at a daily dose of the lutein of at least 0.005 mg/kg body weight.

In an embodiment, the macular carotenoid composition is administered at a daily dose of the zeaxanthin isomer(s) of at least 0.001 mg/kg body weight.

In an embodiment, the macular carotenoid composition is administered at a daily dose of the lutein of at or about 0.005 mg/kg body weight.

In an embodiment, the macular carotenoid composition is administered at a daily dose of the zeaxanthin isomer(s) of at or about 0.001 mg/kg body weight.

In an embodiment, the macular carotenoid composition is administered at a daily dose of the combination of at or about 0.005 mg/kg of the lutein, and at or about 0.001 mg/kg body weight of the zeaxanthin isomer(s) to such a subject.

In an embodiment, the macular carotenoid composition is administered at a daily dose of at or about 0.0005 mg/kg of the lutein or at least 0.0005 mg/kg of the lutein to such a subject.

In an embodiment, the macular carotenoid composition is administered at a daily dose of at or about 0.0001 mg/kg body weight of the zeaxanthin isomer(s) or at least 0.0001 mg/kg of the zeaxanthin isomer(s) to such a subject.

In an embodiment, the macular carotenoid composition is administered at a daily dose of the combination of at or about 0.0005 mg/kg of the lutein, and at or about 0.0001 mg/kg body weight of the zeaxanthin isomer(s) to such a subject.

In an embodiment, the macular carotenoid composition is administered at a daily dose of the combination of at least 0.0005 mg/kg of the lutein, and at least 0.0001 mg/kg body weight of the zeaxanthin isomer(s) to such a subject.

In an embodiment, the macular carotenoid composition is administered at a daily dose of the lutein of at least 0.025 mg/kg body weight.

In an embodiment, the macular carotenoid composition is administered at a daily dose of the zeaxanthin isomer(s) of at least 0.005 mg/kg body weight.

In an embodiment, the macular carotenoid composition is administered at a daily dose of the combination of the lutein of at least 0.025 mg/kg body weight, and the zeaxanthin isomer(s) of at least 0.005 mg/kg body weight.

In an embodiment, the macular carotenoid composition is administered at a daily dose of the lutein of at least 0.05 mg/kg body weight.

In an embodiment, the macular carotenoid composition is administered at a daily dose of the zeaxanthin isomer(s) of at least 0.01 mg/kg body weight.

In an embodiment, the macular carotenoid composition is administered at a daily dose of the combination of the lutein of at least 0.05 mg/kg body weight and the zeaxanthin isomer(s) of at least 0.01 mg/kg body weight.

In an embodiment, the macular carotenoid composition is administered at a daily dose of the lutein of at least 0.1 mg/kg body weight.

In an embodiment, the macular carotenoid composition is administered at a daily dose of the zeaxanthin isomer(s) of at least 0.02 mg/kg body weight.

In an embodiment, the macular carotenoid composition is administered at a daily dose of the combination of the lutein of at least 0.1 mg/kg body weight and the zeaxanthin isomer(s) of at least 0.02 mg/kg body weight.

In an embodiment, the macular carotenoid composition is administered at a daily dose of the lutein of at or about 0.025 mg/kg body weight.

In an embodiment, the macular carotenoid composition is administered at a daily dose of the zeaxanthin isomer(s) of at or about 0.005 mg/kg body weight.

In an embodiment, the macular carotenoid composition is administered at a daily dose of the combination of the lutein of at or about 0.025 mg/kg body weight and the zeaxanthin isomer(s) of at or about 0.005 mg/kg body weight.

In an embodiment, the macular carotenoid composition is administered at a daily dose of the lutein of at or about 0.05 mg/kg body weight.

In an embodiment, the macular carotenoid composition is administered at a daily dose of the zeaxanthin isomer(s) of at or about 0.01 mg/kg body weight.

In an embodiment, the macular carotenoid composition is administered at a daily dose of the combination of the lutein of at or about 0.05 mg/kg body weight and the zeaxanthin isomer(s) of at or about 0.01 mg/kg body weight.

In an embodiment, the macular carotenoid composition is administered at a daily dose of the lutein of at or about 0.1 mg/kg body weight.

In an embodiment, the macular carotenoid composition is administered at a daily dose of the zeaxanthin isomer(s) of at or about 0.02 mg/kg body weight.

In an embodiment, the macular carotenoid composition is administered at a daily dose of the combination of the lutein of at or about 0.1 mg/kg body weight and the zeaxanthin isomer(s) of at or about 0.02 mg/kg body weight.

In an embodiment, the macular carotenoid composition is administered at a daily dose at least 0.05 mg/kg body weight of the lutein or lutein isomer such as t-lutein, and/or at least 0.01 mg/kg body weight of the zeaxanthin isomer(s), such as meso-zeaxanthin and R,R zeaxanthin, either alone or in combination.

In an embodiment, the macular carotenoid composition is administered at a daily dose of the lutein of at least 0.001 mg/kg body weight.

In an embodiment, the macular carotenoid composition is administered at a daily dose of the zeaxanthin isomer(s) of at least 0.005 mg/kg body weight. In an embodiment, the macular carotenoid composition is administered at a daily dose of the zeaxanthin isomer(s) of at least 0.0002 mg/kg body weight.

In an embodiment, the macular carotenoid composition is administered at a daily dose of the combination of the lutein of at least 0.001 mg/kg body weight and the zeaxanthin isomer(s) of at least 0.005 mg/kg body weight, or at least 0.0002 mg/kg body weight.

In an embodiment, the macular carotenoid composition is administered at a daily dose of the lutein of at or about 0.001 mg/kg body weight.

In an embodiment, the macular carotenoid composition is administered at a daily dose of the zeaxanthin isomer(s) of at or about 0.005 mg/kg body weight. In an embodiment, the macular carotenoid composition is administered at a daily dose of the zeaxanthin isomer(s) of at or about 0.0002 mg/kg body weight.

In an embodiment, the macular carotenoid composition is administered at a daily dose of the combination of the lutein of at or about 0.001 mg/kg body weight and the zeaxanthin isomer(s) of at or about 0.005 mg/kg body weight, or at or about 0.0002 mg/kg body weight.

It will be appreciated that any of the mg/kg values stated above can represent a lower limit in a range of the mg/kg amount of the respective carotenoid (i.e. the lutein and/or zeaxanthin isomer(s)) present in the dose. It will also be appreciated that any of the mg/kg values above can represent an upper limit of the mg/kg amount of the respective carotenoid, either alone, or where relatively higher mg/kg values can be used as an upper limit in a range together with one of the relatively lower mg/kg values described above as the lower limit.

In an embodiment, the macular carotenoid composition includes along with the active ingredient(s), e.g. carotenoid(s), at least one food grade excipient as described herein.

In an embodiment, the methods herein include evaluating overall health status after the administration of the macular carotenoid composition.

An embodiment herein is directed to a method of identifying a subject in need thereof to increase MPOD, by administering a macular carotenoid composition to such a subject in an effective daily dose and evaluating an improvement of optical density and/or of distribution of macular pigments.

The higher the level of MPOD, the better protection one has against retinal damage from blue light and oxidative stress. The MPOD is associated with brain function, executive function, and processing speed. The layer of macular pigment is located in the inner retina, and it is remote from the metabolic activities involved in the pathogenesis of age-related macular degeneration (AMD) which occur in the outer retina. The generation of radical oxygen species (ROS) in retinal pigment epithelium (RPE) cells and the resulting increase in oxidative retinal stress in the outer retina. When ROS levels exceed the RPE cell's antioxidative capacity, the result is increased levels of retinal oxidative stress and increased inducement of the inflammatory response. The antioxidant enzymes superoxide dismutase (SOD), catalase, glutathione peroxidase and glutathione reductase, for example, display reduced activities in the brains. A decline in the normal antioxidant defense mechanisms can increase the vulnerability of the brain to the deleterious effects of oxidative damage. ROS can cause severe damage to mitochondrial and cellular proteins, lipids, and nucleic acids and increase psychological and physiological stress.

In an embodiment, a macular carotenoid composition may be administered on a daily basis in an effective amount, such as for example at a mg/kg body weight dose of each lutein and/or meso-zeaxanthin, and at a mg/kg body weight dose of zeaxanthin (e.g. R,R-zeaxanthin), and then evaluating reduction of psychological stress and associated hormones and conditions by co-relating the administered amount(s) of the carotenoid(s) with an improvement in optical density or distribution of macular pigments.

In an embodiment, a macular carotenoid composition may be administered on a daily basis in an effective amount, such as for example at levels of 6 mg to 30 mg/day of the active ingredient(s), for a period of 1 to 12 months or longer, and assessing the parameters for evaluation of reduction in psychological and physiological stress at least at baseline, around 6 months, and around 12 months, and annually thereafter.

In an embodiment, 6 mg to 20 mg daily dose of trans-lutein corresponds to administration of a macular carotenoid composition at a dose of at least 0.05 mg/kg body weight of lutein. It will also be appreciated that a daily dose of at least 0.01 mg/kg body weight of the zeaxanthin isomer(s) (e.g. meso- and/or R,R-) can also be included. See reported example below.

In an embodiment, the daily dose may be in the range of 1 mg to 50 mg of lutein (e.g. trans-lutein). In an embodiment, the daily dose may also include an amount of zeaxanthin isomer(s). In an embodiment, the amount of zeaxanthin isomer(s) can be about 0.12 mg. In an embodiment, the amount of zeaxanthin isomer(s) can be about 0.9 mg of meso-zeaxanthin and 0.3 of R,R-zeaxanthin. In an embodiment, other doses of lutein can be 10 mg and 20 mg, where the amount of zeaxanthin isomer(s) can be adjusted accordingly.

In an embodiment, the period of administration is at least one month. It will be appreciated that the period of administration can be continued for a period till the stress management is evident through MPOD improvement, cortisol reduction and other parameters. It will also be appreciated that administration can be taken for extended time periods, without any side effects or harmful reactions in the body. It will also be appreciated that the evaluation can be done at 0 time, which is baseline, while monthly and/or quarterly evaluations can be continued for a year or longer until the suitable stress management is achieved and/or risk factors are managed.

An embodiment includes administering to a subject in need thereof, an effective amount of a daily dose of lutein and/or zeaxanthin isomer(s) and evaluating reduction in physiological stress by co-relating the administered amount(s) of the carotenoid(s) with a reduction in cortisol levels. For example, the daily dose includes lutein, meso-zeaxanthin, and R,R-zeaxanthin.

An embodiment also includes administering to a subject in need thereof, an effective amount of a daily dose of at least 6 mg of the active ingredient(s) of the macular carotenoid composition and assessing the levels of serum lutein and zeaxanthin isomers, blood cortisol levels and macular pigment optical density (MPOD) via relevant techniques. Behavioral data are also obtained via questionnaire to assess psychological stress, anxiety and depression in the subjects administered with the macular carotenoid composition.

The term 'co-relating' herein includes a response observed in subjects after administration of the specific doses of a composition that is proportional, e.g. directly proportional, to the improvement in optical density or distribution and/or reduction in cortisol levels, thus dose and effect can be co-related to each other. Co-relation between the dose and effect (response) can be observed through effect of various doses on MPOD, e.g. at baseline, subjects' estimation of their level of psychological stress was significantly correlated to their retinal lutein status. To check effect of carotenoid supplementation on stress reduction, subjects' psychological stress measures were evaluated at the final study visit, for example at about 12 weeks and compared to their baseline levels. Psychological stress was found to be significantly reduced in the groups administered with the compositions corresponding to 10 and 20 mg of t-lutein, but not in group which received 6 mg dose or placebo group. Hence there is a co-relation between levels of carotenoid administered and the effect observed. It may be also that at some level beyond a 20 mg daily dose, retinal response to carotenoid supplementation levels off.

In an embodiment, a method for managing stress in a subject in need thereof, includes administering an effective amount of a macular carotenoid composition, evaluating management of psychological and physiological stress by improvement in macular pigment distribution and/or density and reduction in cortisol levels, thus improving overall health status of a subject.

The macular carotenoid compositions and methods described herein impact on three physiological systems that are involved in the stress response, which include the nervous system, the endocrine system, and the immune system.

The macular carotenoid compositions herein in some embodiments are comprised of at least one xanthophyll carotenoid selected from the group consisting of lutein and lutein isomers including t-lutein, zeaxanthin isomers including zeaxanthin (e.g. R,R-zeaxanthin) and meso-zeaxanthin, and the like, enantiomers, metabolites, esters, salts, derivatives thereof, and combinations thereof, along with at least one food grade excipient, for example fat, fatty acid, oil, antioxidant, vitamin, and the like and combinations thereof.

Embodiments include methods of identifying a subject in need thereof, administering a daily dose of lutein and/or zeaxanthin isomer(s), along with at least food grade excipient, to a subject experiencing, suffering and/or likely to have stress and evaluating overall health status.

Macular carotenoid compositions herein can provide methods of managing stress of a subject by administering a daily dose of lutein either alone or in combination with effective doses of zeaxanthin isomer(s). These carotenoids may be administered alone or in combination with each other and/or in combination with at least one food grade excipient, for example a fat, fatty acid, oil, antioxidant and the like, and combinations thereof, to a subject.

In an embodiment, a macular carotenoid composition may be administered on a daily basis in an effective amount, such as for example at levels of the active ingredient(s) of at least 6 mg to 30 mg/day for a period of 1 to 12 months and assessing the parameters for evaluation of reduction in psychological and physiological stress at baseline, 6 months and 12 months.

In an embodiment, methods herein include administering to a subject in need thereof with an effective amount of a macular carotenoid composition comprising macular carotenoids selected from at least one of lutein, lutein isomers, zeaxanthin, isomers of zeaxanthin, including meso-zeaxanthin, salts, metabolites, derivatives or combinations thereof.

In an embodiment, methods herein include administering an effective amount of a macular carotenoid composition comprising at least or about 85% by weight of total xanthophylls to an individual in need thereof suffering from stress. The xanthophylls may contain trans-lutein at least 80% by weight, (R,R)-zeaxanthin at or about 6% by weight, and (R,S)-zeaxanthin at or about 6% by weight being, and the remaining concentration may be other carotenoids. In an embodiment, the amount of trans-lutein can be at or about 80% by weight or higher than 80% by weight.

In some embodiments, macular carotenoid compositions herein can include a minimum of at or about 67% by weight lutein and a minimum of at or about 13.5% by weight zeaxanthin isomers, including meso-zeaxanthin and R,R zeaxanthin.

In an embodiment herein an effective daily dose of a macular carotenoid composition for management and treatment of a subject, experiencing, suffering or likely to be affected by physiological stress and/or psychological stress, or conditions of the like hampering routine activities and overall well-being.

The term 'treatment' refers to the condition wherein the subject suffering from stress, may be psychological, physiological and/or chronic is identified by relevant techniques and the macular carotenoid compositions as described herein, are administered in effective doses to such individual over a period of time, in order to treat his/her condition and to also take care of risk factors associated with the stress condition. The subject who is in need of such treatment can be also identified by asking a set of questionnaire, which give indication about overall health status and thus sets ahead need for treatment of such subject.

The term 'prevention' or 'prophylaxis' refers to administering the macular carotenoid compositions described herein, in an effective amount to subjects who do not show any current symptoms of stress, but are prone to psychological, physiological or chronic stress due to hectic routine, work pressure, family conditions, health problems, social status. As the macular carotenoid compositions can be used as nutritional supplements over a prolonged time without any side effects, these can be administered to such subjects as a prophylactic or preventive measure.

The term "manage, managing, or management of stress" as used herein, unless otherwise indicated, describes controlling and improving health conditions of a subject in need thereof, in terms of improving the associated risk factors based on such stress, which affect routine daily activities and additional work load, thus lowering the output expected from an individual. The stress may be physiological, psychological or any other related type of stress. Physiological stress may arise because of chronic or acute diseases, thus affecting specific body organs. This may be experienced by subjects suffering from ailments like diabetes, hypertension, and/or cancer, thus affecting other body systems. The psychological stress may affect number of physiological functions and activities of an individual under stress. One of the risk factors may be hampering visual performance or overall well-being of an individual, which is due to lowering of density of macular pigments (MPOD) or disturbing the distribution of macular pigments in a subject's eye. Another risk factor may be increase in blood cortisol levels or oxidative or inflammatory markers, which are indicative of psychological stress. Improving or reducing one or more of these risk factors by administering an effective amount of a the macular carotenoid composition herein can help in reducing stress and to improve overall health status of a subject, who is in need of such treatment. Macular carotenoid compositions and methods as used herein, encompasses both a prophylactic and therapeutic regimen and also includes self-treatment (e.g. a subject without the assistance of any intermediary ingests or applies a carotenoid to himself or herself).

In an embodiment, the macular carotenoid compositions herein can improve density and/or distribution of macular pigments in an eye, thus relieving stress in a subject in need thereof. Macular carotenoid compositions herein can also reduce stress by reducing cortisol levels in blood.

Embodiments herein can improve overall health status of a subject after administration of macular carotenoid composition(s) herein, and the improvement may be evaluated through the questionnaire and recording the feedback of the subjects Macular carotenoid compositions herein are safe for consumption and can be employed for management of relieving psychological and/or physiological stress as well as associated risk factors when administered in an effective amount to a subject in need thereof. The reduction in stress is shown by improvement in density and distribution of macular pigment as well as reduction in blood cortisol levels, which ultimately results in improvement in overall health status and well-being of a subject.

Applicant has carried out rigorous experimentation for the evaluation of effect(s) of macular carotenoid composition on healthy volunteers as well as subjects suffering from stress and found that it is effective in increasing MPOD levels, reducing cortisol levels, reducing anxiety and depression, thus managing stress and improving overall health status, when administered in an effective daily dose.

Stress in a subject can be co-related with reduced or disturbed density and/or distribution of macular pigments in retina of a subject, where administration of an effective amount of macular carotenoid composition(s) herein can improve density and/or distribution of macular pigments, thus managing or relieving psychological stress and improving overall health status.

In embodiments herein, stress in a subject is also co-related with increase in cortisol levels in a subject and administration of macular carotenoid composition(s) herein in an effective daily dose, reduces the cortisol level, thus relieving physiological stress in a subject.

In one embodiment herein, stress in a subject is also presented in the form of anxiety or depression, or disturbed overall health status, which is seen to be taken care of by administering an effective amount of the macular carotenoid composition over a period of at least 1 to 12 months, and evaluating behavioral data by using relevant questionnaire to assess psychological stress such as anxiety and depression, in healthy subject, and/or in a subject in need thereof.

In an embodiment, a method for identifying a subject likely to have stress includes administering an amount of a macular carotenoid composition sufficient to reduce stress. Macular carotenoid compositions herein may be administered in a daily effective dose of lutein and/or zeaxanthin isomer(s) to an identified subject likely to have stress.

Macular carotenoid compositions herein are comprised of macular pigment(s) at least one selected from the group of lutein, zeaxanthin and/or their isomers, such as t-lutein, R,R-zeaxanthin, meso-zeaxanthin, and/or salts, metabolites, and derivatives thereof, and the like, which may be derived for example from plant extract and/or oleoresin containing xanthophylls and/or xanthophylls esters, and are useful for nutrition and health applications.

In one embodiment, a macular carotenoid composition is comprised of total xanthophylls. The composition may include at least 80% by weight being trans-lutein, at or about 6% by weight being (R,R)-zeaxanthin and at or about 6% by weight being (R,S)-zeaxanthin. The remaining may be other carotenoids. The macular carotenoid composition is administered to a subject in need thereof suffering from psychological, physiological or any other type of stress.

The macular carotenoid compositions herein can be in the form of delivery systems, which are convenient for administration and ensure dose accuracy and efficacy, such as powder, granules or beadlets for reconstitution in a suitable vehicle or beverage medium, tablets, capsules, oil suspensions, soft gel capsules, meant for oral administration, as well as semisolid and liquid formulations for other than enteral routes of administration. The delivery of the macular carotenoid compositions or preparations can be packaged and used in, for example, flavoring mixtures that also contain salt or other spices for use in flavoring foods such as for example but not limited to soups, salads, popcorn, casseroles, and the like, baking mixes for use in preparing cakes, cookies, brownies, and the like, dried soup mixes, additives for milk such as chocolate-flavored powders, and other granular formulations, such as but not limited to functional foods and beverages. The delivery system may include an enteric coating, a sustained release coating, and/or a release control coating. The delivery system may release lutein and/or meso-zeaxanthin, and zeaxanthin about 10 minutes to 12 hours from the time of administering the composition to the subject.

Macular carotenoid compositions described herein can relieve or manage psychological, physiological and chronic stress and also reduce anxiety and depression, thus improving overall health status of healthy individual or a subject suffering from stress.

Macular carotenoid compositions described herein can relieve or manage physiological stress and improve overall health status by reducing cortisol levels in the blood.

Macular carotenoid compositions herein can also improve distribution and density of macular pigments in the eyes, thus improving visual performance of a subject in need thereof, thus relieving or managing psychological stress.

Macular carotenoid compositions herein can be administered to a subject for periods of 1 to 12 months and maintain higher levels of serum carotenoids, thus resulting into reduction in oxidative stress and inflammation, beneficial for reducing stress, cortisol levels and anxiety.

Macular carotenoid compositions herein are safe for consumption and can be employed for management, treatment or prevention of stress as well as the associated risk factors of stress, and to improve overall health status of a subject, when administered in effective amounts over prescribed time period.

DETAILED DESCRIPTION

Figure 1:
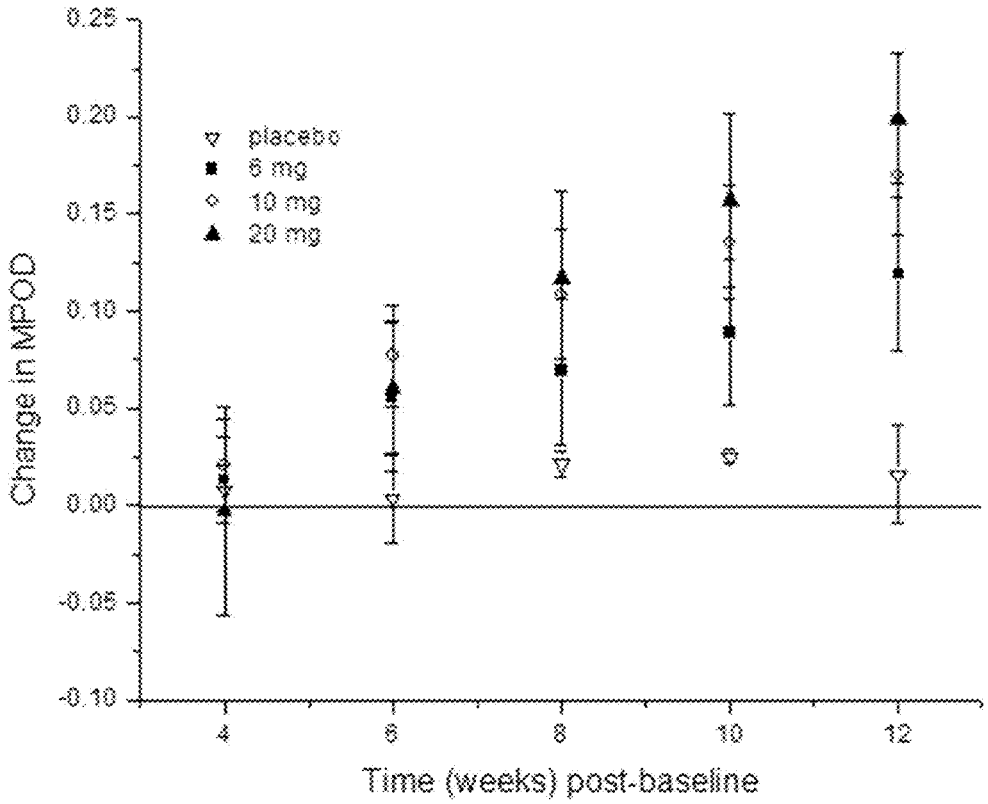
FIG. 1 shows a graph of the response to different levels of daily carotenoid composition, versus placebo.

The following terms, among others, are used to describe the macular carotenoid compositions and methods herein. It is to be understood that a term which is not specifically defined is to be given a meaning consistent with the use of that term within the context of the macular carotenoid compositions and methods herein and as understood by those of ordinary skill.

The term "subject" is used throughout the specification within a context to describe a mammal, an animal or a human being, to which management, treatment, and/or prevention including prophylactic treatment (and prophylaxis), with macular carotenoid compositions herein is provided. For management, treatment and/or prophylaxis of those conditions, specific parameters or disease states which are specific for human beings to generate stress are considered. Human beings may be subjected to various conditions such as changes in routine, extra work load, disturbed family conditions and relationships and the like conditions which affect normal functioning of such subject. Chronic and disease conditions such as diabetes, hypertension, systemic and local infections, cancer, physical injury, and the medical treatment thereof may also cause stress in individuals. Aside from applications for humans, the macular carotenoid compositions herein have additional uses in the veterinary world. Conditions under which animals would benefit due to administration of macular carotenoid compositions herein are particularly those which are subjected to stress due to training procedures and education for specific purposes, e.g. for hunting dogs, guide dogs, police dogs, etc., or animals used in the movie industry. Animals which can benefit from macular carotenoid compositions herein include those animals which are subject to stressful conditions such as, for example, after capture or transport or may be due to housing conditions such as change of domicile or owner. Animals which are subject to stress would also include those which are racing animals (e.g. dogs, horses, camels), or used in various sports, performing animals (such as circus animals and those appearing on stage, television or in the movies) and horses which perform dressage and other highly disciplined routines. Preferred "animals" may include but are not limited to pets or companion animals and farm animals. Examples of pets are dogs, cats, birds, aquarium fish, guinea pigs, (jack) rabbits, hares, and ferrets. Examples of farm animals are aquaculture fish, pigs, horses, ruminants (cattle, sheep and goats), and poultry.

The term "effective amount" is used herein, unless otherwise indicated, to describe an amount of a compound or composition which, in context, is used to produce or affect an intended result, whether that result relates to the management of a subject's stress by improving overall health status. These amounts may reflect specific concentrations of active ingredient(s) which are present as part of a total composition, when the doses are measured as an amount(s) corresponding to individual nutrient(s) such as lutein, lutein isomers, zeaxanthin, meso-zeaxanthin, and/or other zeaxanthin isomers, as present in the composition The doses administered per kg body weight corresponding to specific nutrient of the composition may vary, but the effect produced by specific doses is measurable qualitatively and/or quantitatively for a particular health application under test. This term subsumes all other effective amount or effective concentration terms (including the term "amount sufficient") which are otherwise described in the present application.

The term "overall health status" refers to the health status of a subject which is a multi-dimensional concept that is usually measured in terms of emotional well-being, physical well-being and satisfactory social functioning. There is no single "standard" measurement of overall health status for individuals or population groups of animals. Subject's overall health status may be measured by an observer (e.g., a physician), who performs an examination and rates the individual along any of several dimensions, including parameters reflecting overall well-being of an individual for sound performance during daily routine activities. The questions that can be asked or effects observed in the subjects under test can be related to assessing nervousness or shakiness inside the body, faintness or dizziness, feeling annoyed or irritated, a troublesome feeling, poor appetite, loneliness, and/or fear of a crowd or situations, and the like. The overall health status is evaluated by asking such questions which are called as Sub-Health Status Questionnaire (SHSQ) and rating the individual responses on a scale and the data are aggregated to assess those tested and for a population.

The term "zeaxanthin" or "zeaxanthin isomers" is used throughout this specification within a context to describe the compositions, and can include RR-zeaxanthin and/or RS-meso-zeaxanthin (meso-zeaxanthin).

The term "macular carotenoids" is used throughout the specification within a context to describe the compositions, and can include lutein and/or zeaxanthin isomers such as R,R-zeaxanthin and/or R,S-meso-zeaxanthin herein.

Therefore the term "subject in need thereof" as used herein, unless otherwise mentioned, means an individual who is suffering from one or more risk factors or symptoms indicating psychological or physiological stress, which may affect normal physiological functions and work conditions. Subjects in need of stress management can be identified by measuring density or distribution of macular pigments in retina of a subject and selecting the subjects having lowered macular pigment optical density or distribution. The subjects are also checked for cortisol levels in the body as more cortisol is generated in the body as an indicator of physiological stress on body system.

The term "macular carotenoid composition" as used herein, unless described otherwise, describes a xanthophyll composition containing macular pigments comprising relatively high amounts of lutein, zeaxanthin, and/or isomers of both thereof, including for example, t-lutein, meso-zeaxanthin, R,R-zeaxanthin, and the salts, metabolites and derivatives thereof, either alone or in combination, and including one or more food grade excipients, such as fatty acid, fatty acid ester, triglyceride, oil, antioxidant, stabilizer and the like.

Some embodiments herein relate to a macular carotenoid composition being a xanthophyll composition containing macular pigments of trans-lutein, zeaxanthin isomers, namely (R,R)-zeaxanthin and (R,S)-zeaxanthin (meso-zeaxanthin) derived from the plant extract and/or oleoresin containing xanthophylls and/or xanthophylls esters, which is safe for consumption and useful for nutrition and health applications. The macular carotenoid composition may be administered in the form which is convenient for administration and ensures dose accuracy, selected from, but not limited to, powders, granules, beadlets for reconstitution, filled as such in sachets, or formulated into tablets, capsules, soft gel capsules, oil suspensions, or formulated as semisolids or liquids for enteric and other routes of administration.

In some embodiments, macular carotenoid compositions herein may be comprised of at least one macular carotenoid selected from the group of, but not limited to, free lutein, lutein ester, lutein isomer, zeaxanthin, zeaxanthin isomers such as meso-zeaxanthin, salts, derivatives, metabolites, and combinations thereof. These carotenoids are formulated by using one or more nutrients or food grade excipients selected from a group of, but not limited to fats, fatty acid, oils, medium chain triglycerides, antioxidant, surfactants, vitamins, diluents, taste masking agents, stabilizers, and the like, and combinations thereof.

The terminology used in the description presented herein is not intended to be interpreted in any limited or restrictive manner, simply because it is being utilized in conjunction with a detailed description of certain specific examples or embodiments. Furthermore, embodiments herein may include several novel features, no single one of which is solely responsible for its desirable attributes or which is essential to practicing the innovations described herein.

In an embodiment, a method is provided for management of stress in a subject, by identifying a subject in need thereof, administering an effective amount of a macular carotenoid composition to such subject and evaluating other risk factors associated with stress and thus improving overall health status of such individual.

In an embodiment, a method of psychological stress management includes: measuring optical density or distribution of macular pigments in the retina of a subject and co-relating it with psychological stress; administering an effective daily dose of a macular carotenoid composition over a period of prescribed time and again measuring the density or distribution of macular pigment in that subject. Increase in optical density or improvement in distribution of macular pigments in retina of a subject, exhibited reduction in stress.

Cortisol is an important hormone in the body, secreted by the adrenal glands and involved in biological functions such as metabolism, psychological function, immune and inflammatory response. In an embodiment, the method of physiological stress management is comprised of: measuring cortisol levels in a subject and co-relating higher cortisol levels as an indicator of physiological stress, administering an effective daily dose of the macular carotenoid composition over a period of prescribed time, measuring the cortisol levels in the subject. Reduction in cortisol levels reflects reduced stress.

The subjects are then evaluated for improvement of overall health status using a questionnaire (SHSQ) and recording the responses to the questionnaire to assess management of psychological and physiological stress.

In an embodiment, the subject in need thereof is administered with an effective amount of a macular carotenoid composition herein, comprised of lutein and/or zeaxanthin isomer(s), as a daily dose, either over a period of prescribed time period or as a nutritional supplement (e.g. in combination with multivitamins and/or mineral supplementation) for a life-long time period, based on a need of a subject. The macular carotenoids are either used alone or in combination with their isomers, salts, metabolites or derivatives thereof, along with one or more nutrients and/or food grade excipients.

As per another embodiment, the subject in need thereof is administered with an effective amount of a macular carotenoid composition as described herein, comprised of at least 6 to 30 mg/day of active ingredient(s) in the macular carotenoid composition and parameters for stress evaluation are monitored at baseline level, at 3 months as well as at the end of 12 months of administration.

According to one more embodiment, macular carotenoid compositions herein include a xanthophyll composition containing at least 80% by weight of total xanthophylls. The xanthopylls may include the trans-lutein at least 80% by weight. The remaining may be zeaxanthin isomers, such as (R,R)-zeaxanthin and/or (R,S)-zeaxanthin, which may be derived from the plant extract and/or oleoresin containing xanthophylls and/or xanthophylls esters. The xanthopylls xanthophyll composition is safe for human consumption and useful for nutrition and health care.

Yet as per another embodiment, the xanthophyll composition is comprised of at least 85% by weight of total xanthophylls. The xanthophylls may include the trans-lutein at or about 85% by weight. The remaining may be zeaxanthin isomers, such as, (R, R)-zeaxanthin and/or (R, S)-zeaxanthin. Further, the xanthophylls may include at or about 80% by weight of trans-lutein, at or about 6% by weight of (R, R)-zeaxanthin, and at or about 6% by weight of (R,S)-zeaxanthin.

The macular carotenoid composition may contain at or about 85% by weight trans-lutein, at or about 4% by weight (R, R)-zeaxanthin, and at or about 5% by weight (R,S)-zeaxanthin derived from the plant extract and/or oleoresin containing xanthophylls and/or xanthophylls esters, which is safe for human consumption. Such macular carotenoid composition may be comprised of trans-lutein content of at least or about 85%, and the ratio of trans-lutein and zeaxanthin isomers is in the range of at or about 4:1 to at or about 6:1. The ratio of the isomers of zeaxanthin is in the range of at or about 80:20 to at or about 20:80.

The macular carotenoid compositions herein can satisfy the safety and regulatory considerations, because of the use of generally recognized as safe (GRAS) reagents and hence, is generally safe for consumption and useful for nutrition and health care.

Macular carotenoid compositions herein are administered to a healthy subject and/or a subject in need thereof, to manage, treat and/or prevent the psychological and/or physiological stress, when administered in daily effective doses. Evaluation of the subjects is carried out by measurement of optical density or distribution of macular pigments in the retina, and/or measurement of cortisol levels in the body and by observing, recording the responses to a questionnaire to assess overall health status of a subject. The levels of serum macular carotenoids are also monitored during and after the period of administering the macular carotenoid composition to the subject. Behavioral pattern of subjects under test and anxiety and/or depression states are evaluated using relevant questionnaire. Macular carotenoid compositions herein may be administered over a prescribed time period or over a prolonged time, such as life-long administration of the macular carotenoid composition as per need of a subject.

In an embodiment, the macular carotenoid compositions described herein are in an oral form, for example, a tablet, a capsule, a soft capsule, granules, liquid, effervescent tablet, etc., a suppository form, an eye preparation form, a nasal preparation form, a topical form, for example ointment, gel, cream, lotion, a patch, a sublingual tablet or patch, etc.

Phlebotomy may be performed and macular pigment optical density (MPOD) is measured via heterochromatic flicker photometry. An eccentric area of fixation in human retina commonly referred to as a preferred retinal locus/loci (PRL) is considered as the "standard" measure and the 30' retinal locus (preferred retinal loci) is used for analysis, wherein visual performance is evaluated after administering an effective amount of a macular carotenoid composition herein.

According to one embodiment, increased MPOD levels are correlated to reduction in stress and improvement in overall health status of a subject, who is administered with an effective amount of a macular carotenoid composition herein. The individuals are also evaluated for blood cortisol levels at regular intervals, and the levels of cortisol are compared with a baseline. Serum lutein and zeaxanthin isomers levels are monitored and measured by HPLC technique. Overall health status of a subject is also evaluated by asking questions to subjects and recording the answers and/or recording observations in certain situations to which the subject is exposed and recording the observations, and assessing the anxiety, depression condition and overall stress management.

While the macular carotenoid compositions and methods herein have been described in terms of specific illustrative embodiments, any modifications and equivalents that would be apparent to those skilled in the art are intended to be included within the scope of the methods and macular carotenoid compositions herein. The details of the methods and macular carotenoid compositions herein, its objects, and advantages are explained hereunder in greater detail in relation to non-limiting exemplary illustrations.

EXAMPLES

Example 1: Trial of Stress Management with Macular Carotenoid Composition for 12 Weeks The purpose of this study using a macular carotenoid composition described herein was to characterize the response dynamics in both blood and retina, for three different daily levels of macular carotenoid composition corresponding to t-lutein in amounts of 6, 10, and 20 mg dose of the active ingredient (i.e. t-lutein), versus a placebo. Data regarding subjects' stress and overall health status were also obtained. The macular carotenoid composition was in a formulation of a soft gelatin capsule and was administered orally. The 6, 10, and 20 mg doses relate to a daily dose in the macular carotenoid composition administered having at least 0.05 mg/kg body weight of lutein and 0.01 mg/kg body weight of zeaxanthin isomers (small amount of zeaxanthin is included, e.g. meso-zeaxanthin and R,R zeaxanthin).

Method of Evaluation:

This study was a double-blind, placebo-controlled 12 week trial. Informed consent was obtained from each subject, and the study adhered to the tenets of the Declaration of Helsinki. Twenty-eight healthy subjects, aged 18-25 years, participated in this study. Subjects were randomly assigned to study groups: placebo (n=5), a macular carotenoid composition corresponding to 6 mg lutein (n=7), a macular carotenoid composition corresponding to 10 mg lutein (n=8), and a macular carotenoid composition corresponding to 20 mg lutein (n=8). Subjects were randomized to different treatments. Each subject had one capsule per day orally for a period of 12 weeks. After being familiarized with the study, subjects were instructed to visit the laboratory every 2 weeks, in order to participate in vision testing and phlebotomy. Phlebotomy was conducted after fasting for about 10 hours, and subjects were given some food (e.g. a bagel or a breakfast bar) and water immediately after the blood sampling. A Macular pigment measurement was conducted shortly thereafter. The spatial profile of MPOD was assessed via heterochromatic flicker photometry, using a device described by Wooten et al. (1999).

Effect of a macular carotenoid composition herein was also assessed by measuring levels of cortisol in blood by administering the doses corresponding to 6- to 20-mg lutein, for 12 weeks to the subjects under test. The baseline and final (12 week) visits also included extensive questionnaires designed to acquire information regarding subjects' diet, health, and psychological stress level. For the health assessment, the Sub-Health Status Questionnaire (SHSQ-25; Wang and Yan, 2012) was utilized to determine overall health status. To ensure that the subjects met the inclusion criteria for participation of this study, biometric data (e.g. height, weight, body fat percentage), as well as health habits data (e.g. whether or not a smoker) of the subjects were obtained at each visit.

In some embodiments, the above 6 mg to 20 mg doses, for example: can also be lutein from 0.06 mg/kg to 0.012 mg/kg for macular carotenoid compositions corresponding to 6 mg of t-lutein, (e.g. corresponding to body weights ranging from 5 kg to 100 kg, infant to obese)

In some embodiments, lutein can be at 0.20 mg/kg to 0.04 mg/kg for macular carotenoid compositions corresponding to 20 mg of t-lutein (calculated for body weights 5 kg to 100 kg); while calculating for zeaxanthin and isomers—can also correspond to 0.012 mg/kg to 0.24 mg/kg corresponding to composition containing 6 mg of t-lutein, which contains not less than 1.2 mg of zeaxanthin isomers.

In some embodiments, lutein can further be at 0.04 mg/kg to 0.8 mg/kg for macular carotenoid compositions containing 20 mg t-lutein and not less than 4 mg zeaxanthin (for weights range 5 kg to 100 kg);

In an embodiment, lutein may range from at or about 0.06 to at or about 4 mg/kg, and zeaxanthin isomers may range from at or about 0.0012 mg/kg to at or about 0.8 mg/kg of zeaxanthin isomers. In an embodiment, such relative amounts are contained in macular carotenoid composition containing 6 to 20 mg of t-lutein.

In an embodiment, such macular carotenoid compositions herein can be administered as a daily dose in a range from at or about 0.01 to at or about 10 mg/kg body weight for lutein, and/or in a range from at or about 0.001 to at or about 1 mg/kg body weight for zeaxanthin isomers.

Results

A. Macular Pigment Optical Density (MPOD) Measurement

The overall results for the MPOD response to the various dose levels of the carotenoid, as a function of time in the study, are shown in FIG. 1. Although data were obtained at week 2, a response in the retina (albeit minor) was not detectable until the second study visit (i.e. week 4), and so the week 4 is the first data point presented for each group. Significant increases from the baseline were determined for the 6 mg group at the 12-week visit ($p=0.046$); for the 10 mg group at weeks 8, 10, and 12 ($p<0.001$), and for the 20 mg group at weeks 8, 10, and 12 ($p<0.001$). Because it is considered to be the "standard" measure, the 30' retinal locus (Preferred retinal loci) was used for this analysis. Although the 30' measure explained the most variance in the data, similar results were found for all retinal loci tested, especially those even closer to the center of the fovea (e.g. 10' and 20' loci). From FIG. 1 it can be seen that the response to each level of composition was roughly linear as a function of time, and the response was shown to be greater as time passed as a function of the level of the carotenoid. The data suggest a significant increase in response with increased doses. The increase with the 10 mg group is closer in magnitude to the increase with the 20 mg group, compared with the increase with the 6 mg group versus the increase with the 10 mg group.

B. Measurement of MPOD and Co-Relation with Psychological Stress

Figure 2:
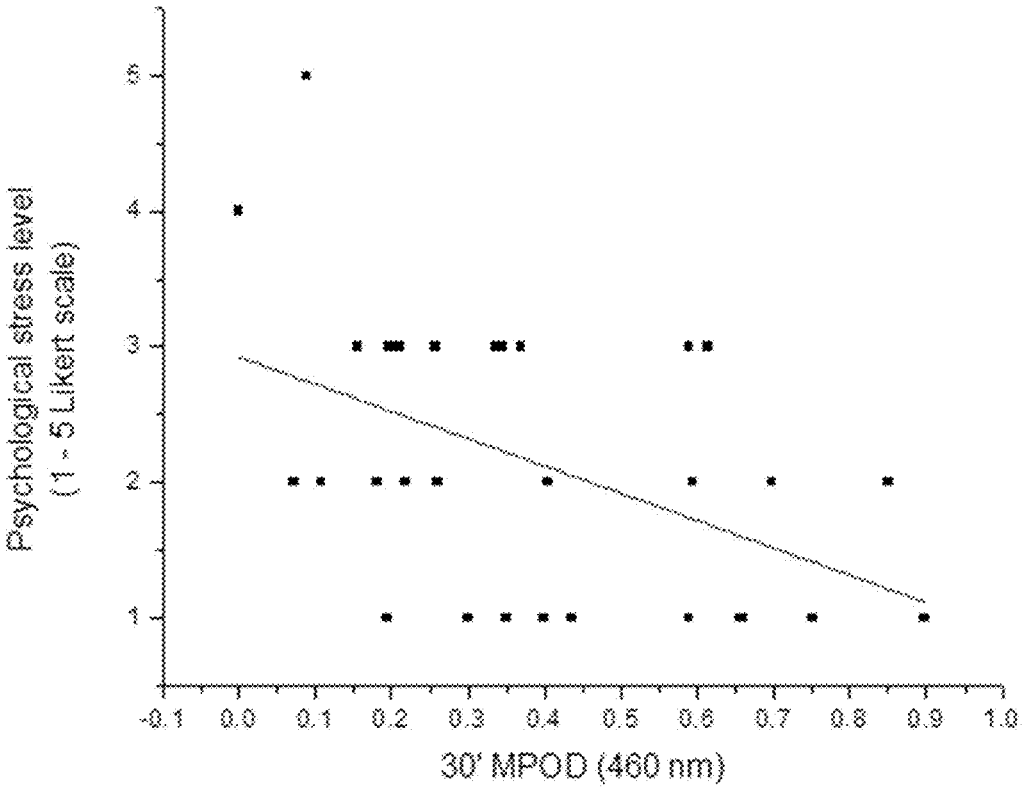
FIG. 2 shows a graph of the subjects' under test and their level of psychological stress at baseline, as a function of macular pigment optical density (MPOD).

Subjects' level of psychological stress was significantly correlated to their MPOD (r=−0.47; p=0.0087; see FIG. 2). In order to determine the potential of macular carotenoid compositions which include for example to 6 to 20 mg of trans-lutein, and which may include in some embodiments combinations with meso-zeaxanthin and/or zeaxanthin (e.g. R,R-zeaxanthin), one example composition tested herein is a Lutemax 2020 composition by Applicant, which is disclosed for example in co-pending U.S. patent application publication 2011/0065805, and which is incorporated by reference herein. Supplementations of such macular carotenoid compositions were evaluated to determine stress reduction, and the subjects' psychological stress were measured at the final study visit (week 12) and compared to their baseline levels.

In other embodiments, macular carotenoid compositions can also include those from Applicant's U.S. Pat. No. 8,212,063, which is incorporated herewith by reference.

TABLE 1

Statistical parameters for baseline and within-subjects lutein effects for both psychological stress and overall health.

| | Baseline relation to MPOD: | | | | | |
|---|---|---|---|---|---|---|
| | Psychological Stress r = −0.47; p = 0.0087 | | | Overall Health r = −0.54; p = 0.002 | | |
| | Paired samples t-test parameters: | | | | | |
| | Average score difference between baseline and final visits | t score | p value | Average score difference between baseline and final visits | t score | p value |
| placebo | −0.4 | −1.633 | 0.322 | 2.8 | 1.91 | 0.215 |
| 6 mg | 0.125 | 0.55 | 0.598 | 4.25 | 2.503 | 0.041 |
| 10 mg | 0.75 | 2.393 | 0.047 | 4.5 | 2.75 | 0.029 |
| 20 mg | 0.889 | 2.409 | 0.032 | 8.111 | 2.438 | 0.047 |

*cell(s) are indicative of statistical significance

FIG. 2 shows the subjects' level of psychological stress at baseline, as a function of MPOD. Red line is least-squares fit to the data (Y=−2.012X+2.92). r=−0.47; p=0.0087.

Paired-sample t-tests were used for this purpose. Psychological stress was found to be significantly reduced in the 10 mg (t=2.393; p=0.047) and 20 mg (t=2.401; p=0.039) groups, but not 6 mg or placebo groups (see Table 1). It appears therefore that the macular carotenoid compositions corresponding to 10 mg and 20 mg of t-lutein account for the significant reduction in the psychological stress.

C. Co-Relation of Improved MPOD with Overall Health Status

Figure 3:
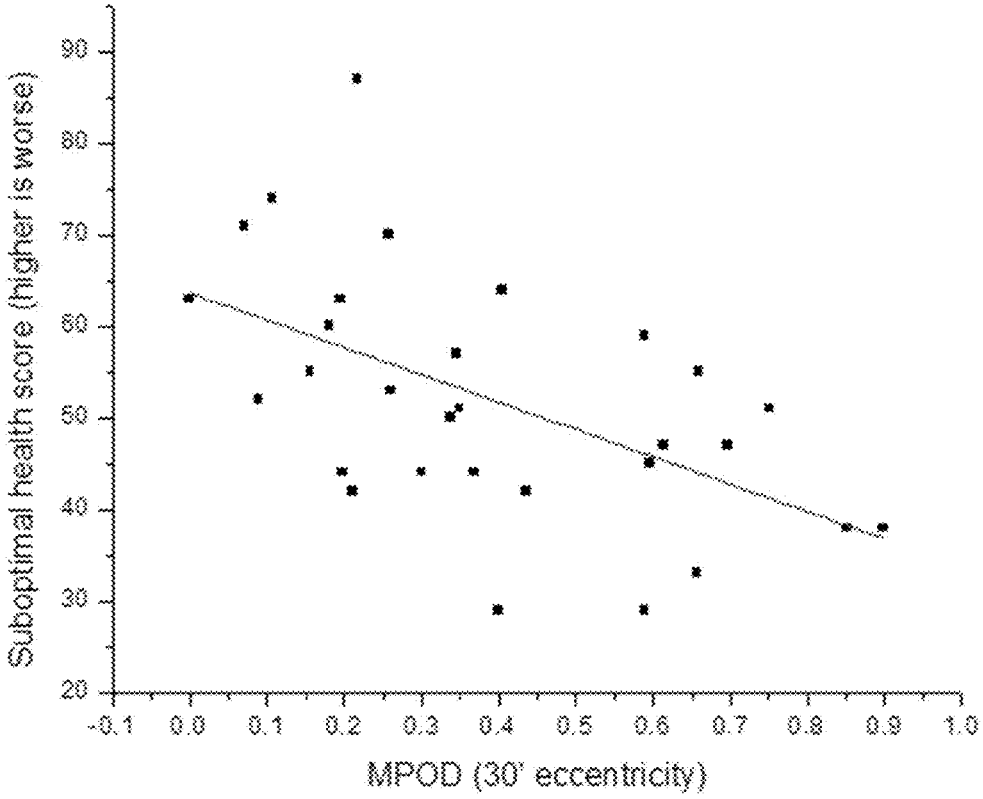
FIG. 3 shows a graph of subjects' overall health status at baseline, as a function of MPOD.

A significant correlation between the retinal lutein status and overall health status (as assessed by the SHSQ-25—see Appendix I) was obtained (r=−0.54; p=0.002; see FIG. 3). As with the psychological stress data, effects of the macular carotenoid composition on overall health status of subjects (as assessed via the SHSQ-25) were determined via comparing their baseline scores to their final visit scores with paired-samples t-tests. At all dose levels of the carotenoid (6, 10, 20 mg of t-lutein (lutein)) in the macular carotenoid compositions, it was found that overall health status improved significantly over the 12 week study period (see Table 1).

Referring to the SHSQ, "SHSQ-25" scores means scores calculated for each respondent by summing the ratings for 25 questions. Although annexure shows more than 50 questions, these are reduced to 25, by combining two questions to form one sentence. Thus total questions asked to the subjects were 25. Each subject was asked to rate a specific statement, based on how often they suffered various specific complaints in the preceding 3 months. The raw scores of 1 to 5 on the questionnaire were recoded as 0 to 4. SHS scores were calculated for each respondent by summing the ratings for the 25 items. The SHSQ is considered as indicative of stress conditions in the subjects, and is used to understand behavioral patterns of a group of subjects, and to understand overall health status of the subjects administered the compositions as described herein.

In FIG. 3, subjects' overall health status at baseline, as a function of MPOD.

The line is a least-squares fit to the data (Y=−29.90X+63.65). r=−0.54; p=0.002.

Figure 4:
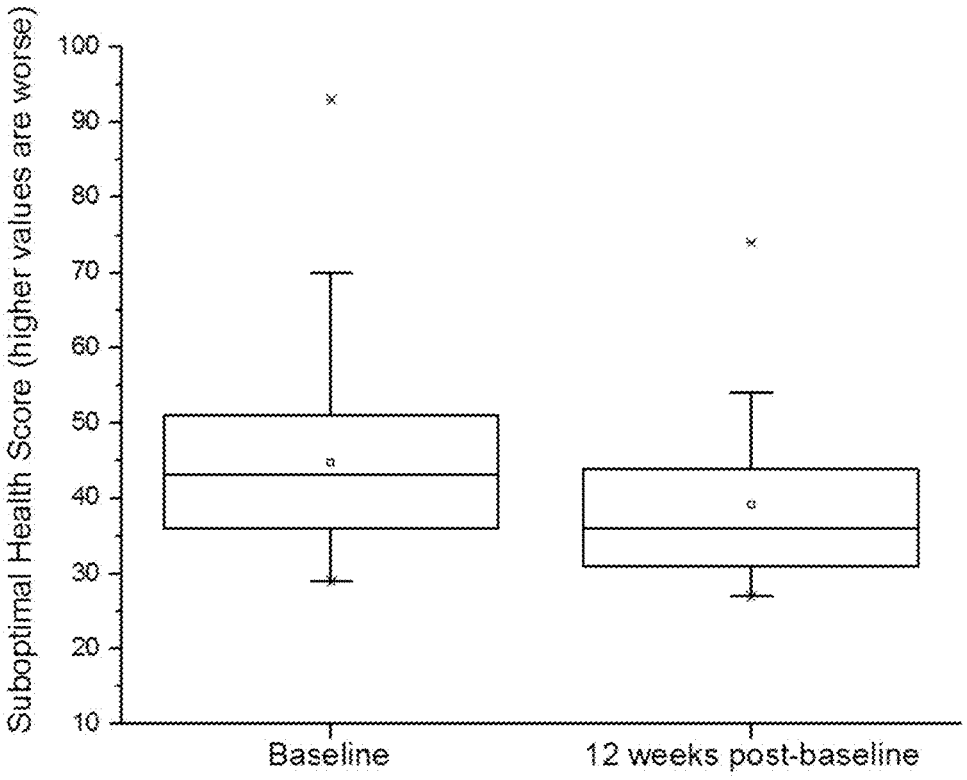
FIG. 4 shows a graph where baseline and final visit SHSQ-25 scores are compared with box-and-whisker plots.

In order to visualize the change in sub-optimal health scores over the 12-week study period, FIG. 4 presents a box-and-whisker plot of the baseline and the final visit data for all 23 lutein supplementation subjects. A paired-samples t-test determined a statistically significant improvement in the overall health status over the study period (t=4.61; p<0.001).

Questionnaires evaluating psychological stress levels, overall health status (suboptimal health questionnaire [SHSQ]), and diet were completed at baseline and final visits.

In addition to a significant decrease in sub-optimal health issues, the subjects also exhibit a markedly reduced score range and its variability in their responses for the 12 week measure versus their baselines (see FIG. 4).

The term sub optimal health issues is related to Sub optimal health questionnaire (SHSQ) provided in Annexure I. A set of questions is prepared which is asked to the study subjects to assess what is the health status before administering the macular carotenoid composition and what is at the end of study, to understand improvement in overall health status of a subject. (Wang W, Yan Y (2012). Suboptimal health: a new health dimension for translational medicine. Clin Transl Med. 14; 1(1):28.).

In FIG. 4, baseline and final visit SHSQ-25 scores are compared with box-and-whisker plots. Asterisks indicate lower and upper range of values, bars are +/−1 standard deviation from the mean.

Figure 5:
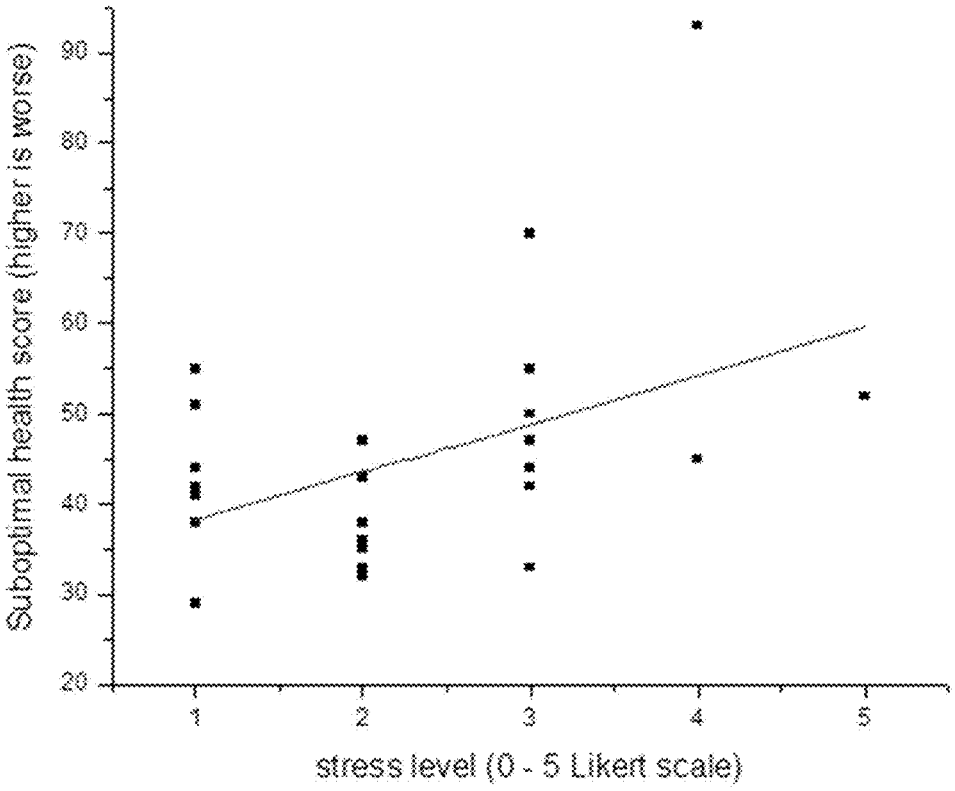
FIG. 5 shows a graph of subjects' overall health status scores, as a function of psychological stress level, at baseline.

In FIG. 5, subjects' overall health status scores, as a function of psychological stress level, at baseline. The line is a least-squares fit to data (Y=5.35X+32.86). r=0.44; p=0.014.

D. Management of Physiological Stress by Cortisol Levels Measurement

It was found that after 12 weeks of the administration of the macular carotenoid composition, blood cortisol levels reduced significantly, which is one of indicators of reducing psychological stress in a subject.

Figure 6:
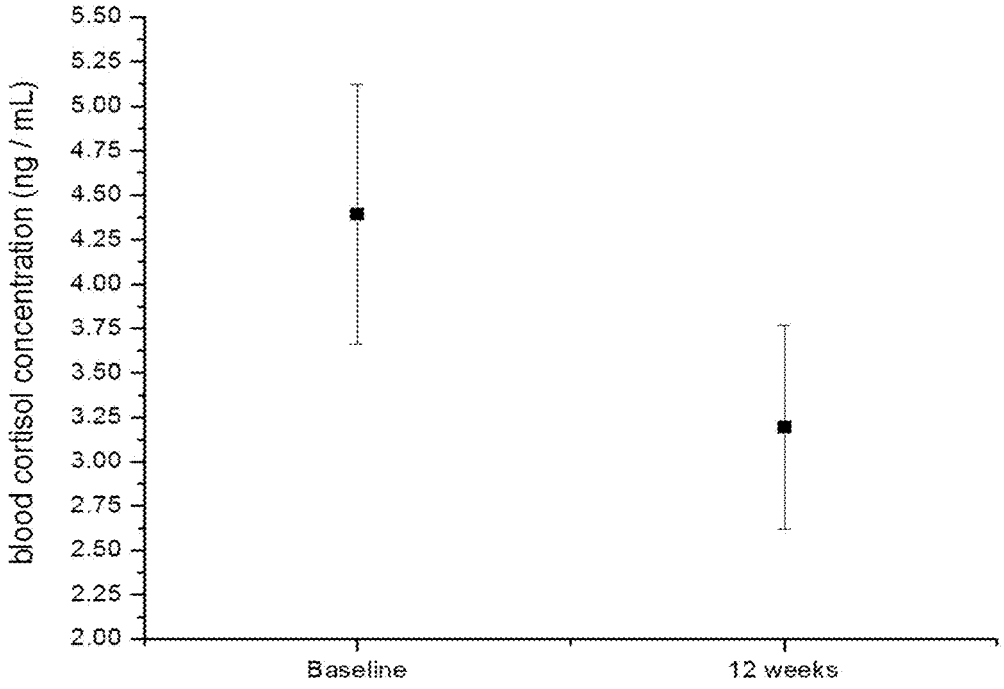
FIG. 6 shows a graph of baseline and 12 weeks effect of composition on blood cortisol concentration.

FIG. 6 shows the baseline and 12 weeks effect of macular carotenoid composition on blood cortisol concentration. In this study, cortisol levels were assessed from pooled subject data to find any changes in cortisol levels before and after administering the macular carotenoid composition described above. ELISA was used to assess blood levels of cortisol. There was a significant effect of the macular carotenoid composition on cortisol levels after 12 weeks of administrating the macular carotenoid composition, compared to the baseline. Baseline cortisol levels were higher in these subjects. There was a significant relationship between the blood cortisol level and psychological stress measure: r=0.661; p=0.0015.

Discussion

MPOD increased significantly in subjects administered with the macular carotenoid compositions herein, compared to a placebo (which exhibited little to no change throughout the trial). Also, it was found that a significant relationship existed between MPOD and psychological stress: r=−0.47; p=0.0087 (more MPOD=lower stress). The retinal response was somewhat linear, with greater increases seen in those taking the higher (e.g. 20 mg) dose of lutein. A repeated-measures analysis of variance (ANOVA) revealed significant increases from the baseline, which were determined with the 6 mg group at the 12-week visit (p=0.046); with the 10 mg group at visits at weeks 8, 10, and 12 (p<0.001), and with the 20 mg group at visits at weeks 8, 10, and 12 (p<0.001). The cross-sectional evaluation of MPOD versus psychological stress revealed a significant relationship between the two, such that the subjects having higher levels of MPOD tended to maintain a lower psychological stress profile (r=−0.47; p=0.0087). After 12 weeks of lutein supplementation, psychological stress levels were found to be reduced significantly in the 10 mg (p=0.047) and 20 mg (p=0.032) groups. The placebo group did not change in this regard. In terms of overall health, the subjects' scores on the SHSQ were found to correlate significantly at the baseline with MPOD, such that those having higher MPOD tended to have fewer health-related problems (e.g. they were sick less often, suffered less from allergies; r=−0.54; p=0.002). After 12 weeks of macular carotenoid composition administration, each group, other than the placebo group, exhibited a significant reduction in health-related problems (6 mg: p=0.041; 10 mg: p=0.029; 20 mg: p=0.047).

In the group administered with the macular carotenoid composition described herein, stress and cortisol were significantly lowered after 10-12 weeks.

Based on the results of this study, ingestion of a macular carotenoid composition herein can produce a significant positive response in a retina. The shapes of the response curves suggest that a response is somewhat linear—higher doses result in a greater response. In terms of systemic/psychological effects, this is the first study to show a relationship between a macular carotenoid composition and psychological stress, and that between a macular carotenoid composition and overall health. These findings have very important implications as an effective, safe, and alternate technique for managing physiological and psychological stress by improving an overall health status.

Macular carotenoid compositions herein have been readily bioavailable, judging from the robust retinal response in subjects. Compared to a placebo, a significant positive response was seen after 12 weeks in the group even with the lowest (6 mg) dose. Moreover, a significant retinal response was seen in the 10- and 20-mg groups after only 8 weeks of administration with a macular carotenoid composition herein. Second, daily administering of a macular carotenoid composition herein corresponding to 10- or 20-mg of lutein significantly reduces psychological stress after 12 weeks of administering the macular carotenoid composition. In our study this effect was seen with the macular carotenoid composition corresponding to two higher doses (10 and 20 mg) of lutein, which indicates that relatively high levels of daily intake can provide effects on psychological stress reduction.

In the group administered with a macular carotenoid composition herein, stress and cortisol was significantly lowered after 10-12 weeks. Scores of overall health status demonstrate significantly improvement over the 12 week study period, for all levels of macular carotenoid compositions (see Table 1), but not for the placebo group. Lastly the results of the study and consideration of relationships of the macular carotenoid composition with both stress and health as shown in FIG. 5 indicate interrelationships among bodily systems (such as the nervous, endocrine, and immune systems), and that the status of these systems can ultimately impact management of physiological and psychological stress.

Example 2: Trial of Stress Management with Composition for Stress 12 Months Trial This 12-month, double-blind, placebo-controlled trial was conducted to evaluate the effects of administering carotenoid on blood cortisol levels, subjects' psychological stress ratings, behavioral measures of mood, and symptoms of suboptimal health.

Method of Evaluation:

59 young (mean age=21.5 yrs.; 27 males), healthy subjects were evaluated in this study. Subjects were randomly assigned to three groups: Group 1 (placebo; n=10), Group 2 (n=24; 12 mg/day total carotenoids, and Group 3 (n=25; 24 mg/day total carotenoids (n=25). All parameters in the study were assessed at baseline, 6 months, and 12 months. Some of the blood markers such as Interleukins, TNF alpha and Brain-derived neurotrophic factor (BDNF) were also evaluated during this supplementation. Total study period was 12 months, the evaluation was done at both 6 and 12 months to check effects at definite intervals BDNF, which is a protein in humans, is encoded by the BDNF gene. BDNF is a member of the neurotrophin family of growth factors, such as the canonical Nerve Growth Factor. Exposure to stress and the stress hormone corticosterone has been shown to decrease the expression of BDNF, and, if exposure is persistent, this leads to an eventual atrophy of the hippocampus.

Supporting this, voluntary exercise, caloric restriction, intellectual stimulation and various treatments for depression increase expression of BDNF in the brain.

Serum lutein and zeaxanthin isomers were measured by high performance liquid chromatography (HPLC), blood cortisol via (ELISA), and macular pigment optical density (MPOD) via customized heterochromatic flicker photometry. Behavioral data were obtained via questionnaire. Psychological stress was determined using the Psychological Stress Measure (PSM-9), scores of anxiety and depression were obtained via the Beck inventories, overall psychological health via the Brief Symptom Inventory (BSI), and symptoms of suboptimal health were evaluated with the Suboptimal Health Status Questionnaire (SHSQ-25).

Figure 7:
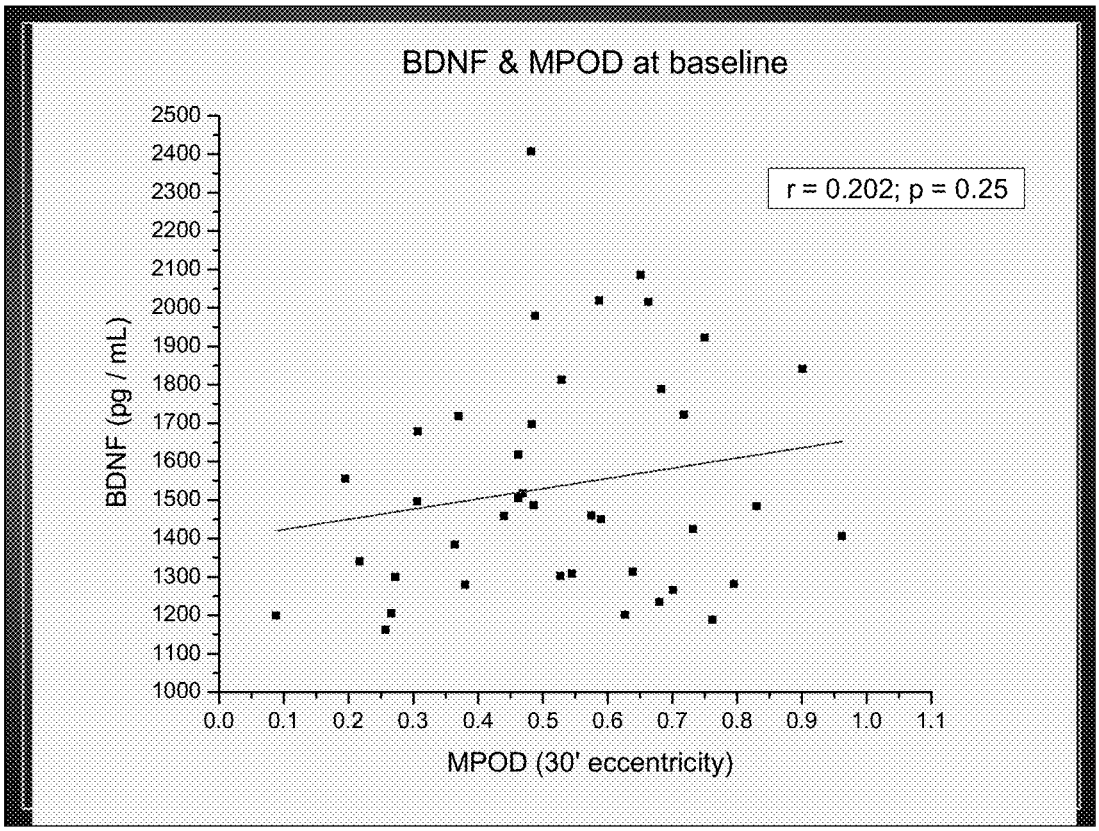
FIG. 7 is a graph of BDNF and MPOD at baseline.

Results:

FIG. 7 shows BDNF and MPOD at baseline (time=0).

Figure 8:
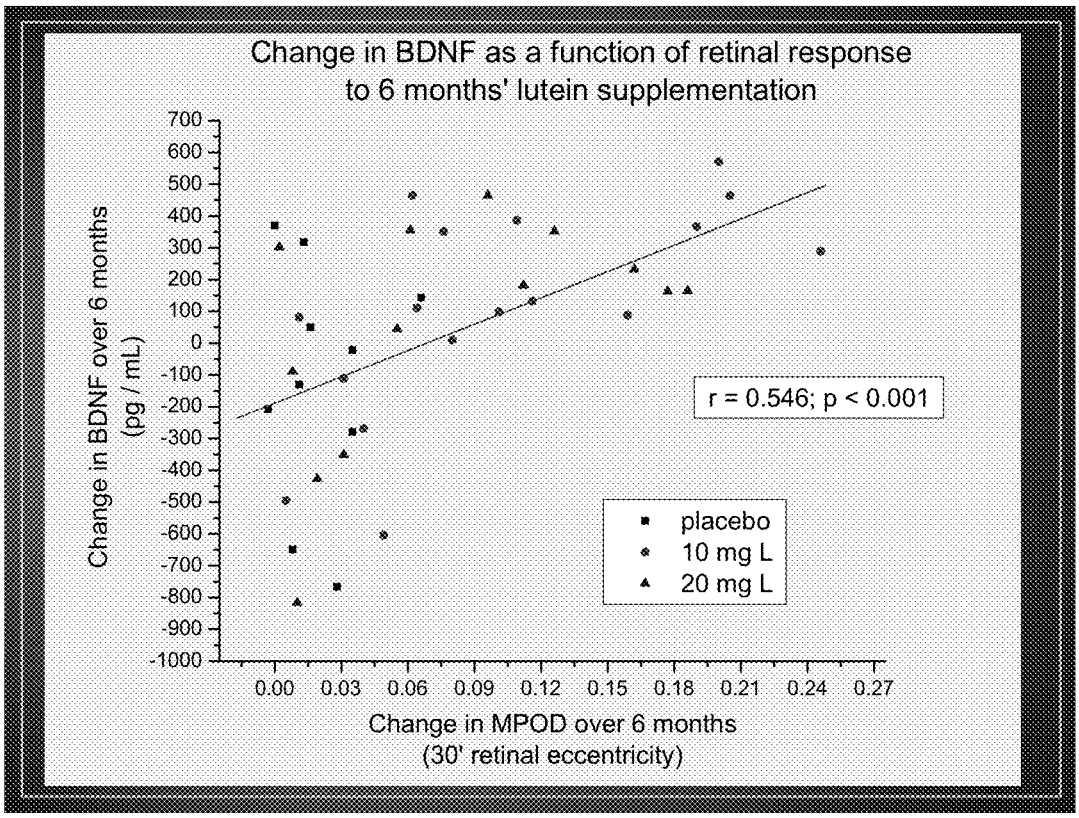
FIG. 8 is a graph of the change in BDNF as a result of 6 months administering carotenoids.

FIG. 8 shows the change in BDNF as a result of 6 months administering carotenoids.

At baseline, BDNF and MPOD expressions were significantly limited and these were increased linearly with the 6 months administering of the composition as shown in FIG. 8.

At baseline, significant correlations were obtained between MPOD and Beck Anxiety scores (r=−0.28; p=0.032), MPOD and BSI scores (r=−0.27; p=0.037), and between blood cortisol levels and PSM-9 scores (r=0.43; p<0.001). Marginally significant correlations were obtained for MPOD and blood cortisol levels (r=−0.202; p=0.124), MPOD and psychological stress (r=−0.218; p=0.10), and MPOD and symptoms of suboptimal health (r=−0.22; p=0.12). After 6 months of administering macular carotenoid, a repeated-measures ANOVA revealed that psychological stress, blood cortisol levels, anxiety scores, and symptoms of suboptimal health were significantly lower for Groups 2 and 3 than those for Group 1 (p<0.01 for all). These outcomes either were maintained at their 6 month levels or decreased further (but not significantly) at 12 months. Serum levels of lutein and zeaxanthin isomers also increased significantly after 6 months (p<0.001) in Groups 2 and 3, and appeared to a plateau thereafter, as indicated by similar values at 12 months to those at 6 months. Group 1 (placebo) did not improve in any of these respects (p>0.65 for all). In Groups 2 and 3, MPOD was found to increase linearly and significantly at both 6 and 12 months (p<0.001). Group 1 exhibited no increase in MPOD across the study period (p=0.710).

Observations: It appears that the administration of the macular carotenoids lutein, zeaxanthin, and meso-zeaxanthin, at levels of at least 12 mg/daily, leads to significant psychological and physiological benefit. Reduction of stress, cortisol, and anxiety is observed after 6 month administering of the carotenoids, and is maintained at 12 months. Trial carried out is for 12 months, means administration of composition for 12 months. During the trials, after 6 months administration, positive effects are observed and the stress reduction continued to be evident after administration for 12 months. This indicates that the effects are not transient, or short-lived. The mechanism for these findings could involve either deposition of carotenoids in neural tissue, the increase in serum levels with administering carotenoids, or both. The effects, however, leveled off after 6 months whereas MPOD continued to increase. It is therefore possible that the reduction of stress, cortisol, and anxiety is dependent upon systemic reduction of oxidative stress and inflammation afforded by relatively high circulating levels of lutein, zeaxanthin, and meso-zeaxanthin. According to this study, the macular carotenoids have been shown to promote wide-ranging, beneficial effects on a number of biological and physiological systems in the body that are themselves impacted by stress (e.g. neural and cardiovascular systems).

Annexure I

Below is one example of a SHSQ (Suboptimal Health Status Questionnaire)

* Begin Instructions and Form*

In order to judge overall health status and to identify the subjects with sub-optimal health (showing symptoms of stress), following questions were asked to the subjects.

Instructions to the Subjects:

Read each of the following items carefully and circle that which best describes how much that problem has distressed or bothered you during the past 7 days including today. Circle only one number for each problem. Do not skip any items. Read the example below before beginning. If you have any questions, please ask the doctor now.

The Questionnaire will now begin.

How much were you distressed by:

| | | |
|---|---|---|
| 1 | Nervousness or shakiness inside | 0 1 2 3 4 |
| 2 | Faintness or dizziness | 0 1 2 3 4 |
| 3 | The idea that someone else can control your thoughts | 0 1 2 3 4 |
| 4 | Feeling others are to blame for most of your troubles | 0 1 2 3 4 |
| 5 | Trouble remembering things | 0 1 2 3 4 |
| 6 | Feeling easily annoyed or irritated | 0 1 2 3 4 |
| 7 | Pains in heart or chest | 0 1 2 3 4 |
| 8 | Feeling afraid in open spaces or on the streets | 0 1 2 3 4 |
| 9 | Thoughts of ending your life | 0 1 2 3 4 |
| 10 | Feeling that most people cannot be trusted | 0 1 2 3 4 |
| 11 | Poor appetite | 0 1 2 3 4 |
| 12 | Suddenly scared for no reason | 0 1 2 3 4 |
| 13 | Temper outbursts that you could not control | 0 1 2 3 4 |
| 14 | Feeling lonely even when you are with people | 0 1 2 3 4 |
| 15 | Feeling blocked in getting things done | 0 1 2 3 4 |
| 16 | Feeling lonely | 0 1 2 3 4 |
| 17 | Feeling blue | 0 1 2 3 4 |
| 18 | Feeling no interest in things | 0 1 2 3 4 |
| 19 | Feeling fearful | 0 1 2 3 4 |
| 20 | Your feelings being easily hurt | 0 1 2 3 4 |
| 21 | Feeling that people are unfriendly or dislike you | 0 1 2 3 4 |
| 22 | Feeling inferior to others | 0 1 2 3 4 |
| 23 | Nausea or upset stomach | 0 1 2 3 4 |
| 24 | Feeling that you are watched or talked about by others | 0 1 2 3 4 |
| 25 | Trouble falling asleep | 0 1 2 3 4 |
| 26 | Having to check and double-check what you do | 0 1 2 3 4 |
| 27 | Difficulty making decisions | 0 1 2 3 4 |
| 28 | Feeling afraid to travel on buses, subways, or trains | 0 1 2 3 4 |
| 29 | Trouble getting your breath | 0 1 2 3 4 |
| 30 | Hot or cold spells | 0 1 2 3 4 |
| 31 | Having to avoid certain things, places, or activities because they frighten you | 0 1 2 3 4 |
| 32 | Your mind going blank | 0 1 2 3 4 |
| 33 | Numbness or tingling in parts of your body | 0 1 2 3 4 |
| 34 | The idea that you should be punished for your sins | 0 1 2 3 4 |
| 35 | Feeling hopeless about the future | 0 1 2 3 4 |
| 36 | Trouble concentrating | 0 1 2 3 4 |
| 37 | Feeling weak in parts of your body | 0 1 2 3 4 |
| 38 | Feeling tense or keyed up | 0 1 2 3 4 |
| 39 | Thoughts of death or dying | 0 1 2 3 4 |
| 40 | Having urges to beat, injure, or harm someone | 0 1 2 3 4 |
| 41 | Having urges to break or smash things | 0 1 2 3 4 |
| 42 | Feeling very self-conscious with others | 0 1 2 3 4 |
| 43 | Feeling uneasy in crowds, such as shopping or at a movie | 0 1 2 3 4 |
| 44 | Never feeling close to another person | 0 1 2 3 4 |
| 45 | Spells of terror or panic | 0 1 2 3 4 |
| 46 | Getting into frequent arguments | 0 1 2 3 4 |
| 47 | Feeling nervous when you are left alone | 0 1 2 3 4 |
| 48 | Others not giving you proper credit for your achievements | 0 1 2 3 4 |
| 49 | Feeling so restless you couldn't sit still | 0 1 2 3 4 |
| 50 | Feelings of worthlessness | 0 1 2 3 4 |
| 51 | Feeling that people will take advantage of you if you let them | 0 1 2 3 4 |
| 52 | Feelings of guilt | 0 1 2 3 4 |
| 53 | The idea that something is wrong with your mind | 0 1 2 3 4 |

0 = Not at all
1 = A little bit
2 = Moderately
3 = Quite a bit
4 = Extremely

*End Instructions and Form*

The invention claimed is:

1. A method for [treatment of] *improving, managing, and/or treating* psychological stress [and] *and/or* physiological stress in a subject, comprising:

a[.]) identifying a subject in need thereof, wherein the subject in need thereof is affected by psychological stress as measured by macular pigment optical density (MPOD) levels [and] *and/or* physiological stress as measured by blood cortisol levels;

b[.]) administering a daily dose of [macular] carotenoid composition in an amount effective for increasing the MPOD levels and reducing the blood cortisol levels over a period of at least one month as compared to those of before the administration of the [macular] carotenoid composition so as to treat stress in the subject, the [macular] carotenoid composition [consists] *consisting* of at least 85% by weight of xanthophylls, the xanthophylls being lutein and zeaxanthin isomers, of which at least 80% by weight being trans-lutein, at least 6% by weight being (R, R)-zeaxanthin and at least 6% by weight being (R, S)-zeaxanthin, wherein the [macular] carotenoid composition consists of at least 0.1 mg/kg body weight of the lutein and, at least 0.01 mg/kg body weight of the zeaxanthin isomers; and c[.]) measuring MPOD [and] *and/or* blood cortisol levels; and d[.]) evaluating an improvement in overall health status of the subject.

2. The method according to claim 1, wherein the subject in need thereof is administered with an effective amount of the [macular] carotenoid composition, *wherein* the [macular] carotenoid composition is derived from the plant extract/oleoresin containing xanthophylls/xanthophylls esters, to improve overall health status of the subject.

3. The method according to claim 1, wherein the subject in need thereof is a mammal.

4. The method according to claim 1, wherein the subject in need thereof is a human.

*5. A method for improving, managing, and/or treating psychological stress in a subject, comprising*

*a) identifying that the subject suffers from psychological stress;*

*b) administering over a period of at least one month a daily dose of carotenoid composition in an amount effective for treating psychological stress in the subject, the carotenoid composition consisting of at least 85% by weight of xanthophylls, the xanthophylls being lutein and zeaxanthin isomers, of which at least 80% by weight is trans-lutein, at least 6% by weight is (R, R)-zeaxanthin and at least 6% by weight is (R, S)-zeaxanthin, the lutein being present in the carotenoid composition in an amount of at least 0.1 mg/kg body weight and the zeaxanthin isomers being present in an amount of at least 0.01 mg/kg body weight;*

*c) measuring one or more markers selected from the group consisting of brain-derived neurotropic factor (BDNF), interleukins, TNF α, blood cortisol level and macular pigment optical density (MPOD) after performing step b); and*

*d) evaluating an improvement in psychological stress in the subject based on the measured marker.*

*6. The method according to claim 5, wherein the psychological stress is selected from the group consisting of cognitive function, memory retention, verbal fluency, and cognitive decline, and a combination thereof.*

*7. The method according to claim 5, wherein identifying that the subject suffers from psychological stress comprises at least one of measuring MPOD in the subject, measuring a blood cortisol level of the subject, and subjecting the subject to a health assessment questionnaire.*

*8. The method according to claim 5, wherein administering the carotenoid composition to the subject improves the one or more markers selected from the group consisting of brain-derived neurotropic factor (BDNF), interleukins, TNF α, blood cortisol level, and macular pigment optical density (MPOD) in the subject as compared to the subject before administration of carotenoid composition.*

*9. The method according to claim 5, wherein the subject is a mammal or human.*

*10. The method according to claim 5, wherein the method further comprises measuring levels of macular pigment optical density (MPOD) in the subject.*

*11. The method according to claim 9, wherein the subject exhibits MPOD below a baseline amount before administering the carotenoid composition, and the method further comprises administering an effective amount of the carotenoid composition to the subject to increase in the amount of levels of MPOD above the baseline amount.*

*12. The method according to claim 5, wherein the carotenoid composition is administered for about 4 weeks to about 12 weeks.*

*13. The method according to claim 5, wherein the carotenoid composition is administered in an amount of about 6 mg/day to about 30 mg/day.*

*14. The method according to claim 5, wherein the carotenoid composition is administered in an amount selected from the group consisting of about 6 mg/day, 12 mg/day and 24 mg/day for a time period selected from the group consisting of about 8 weeks, about 10 weeks, and about 12 weeks.*

*15. The method according to claim 5, wherein the carotenoid composition is administered for at least 6 months.*

*16. A method for improving, managing, and/or treating psychological stress and/or physiological stress in a subject, comprising:*

*a) testing the subject to determine that the subject suffers from psychological and/or physiological stress, based on a measured stress parameter;*

*b) over a period of at least one month administering a daily dose of carotenoid composition in an amount effective for changing the stress parameter to indicate that the subject suffers from reduced stress compared to before the administration of the carotenoid composition, the carotenoid composition consisting of at least 80% by weight of xanthophylls, the xanthophylls being lutein and zeaxanthin isomers, of which at least 80% by weight is trans-lutein, (R, R)-zeaxanthin and (R, S)-zeaxanthin being present in a ratio of between 80:20 and 20:80, wherein the carotenoid composition consists of at least 0.1 mg/kg body weight of the lutein and, at least 0.01 mg/kg body weight of the zeaxanthin isomers; and*

*c) measuring the stress parameter to evaluate physiological and/or psychological stress after step b); and*

*d) evaluating an improvement in overall health status of the subject.*

*17. The method according to claim 16, wherein the stress parameter comprises at least one of macular pigment optical density (MPOD) level, score on a health status questionnaire, and blood cortisol level.*

*18. The method according to claim 16, wherein the xanthophylls further comprise at least 6% by weight (R, R)-zeaxanthin and at least 6% by weight (R, S)-zeaxanthin.*

* * * * *